United States Patent
Chaffin et al.

(10) Patent No.: US 11,548,974 B2
(45) Date of Patent: *Jan. 10, 2023

(54) MODIFIED POLYISOBUTYLENE-BASED POLYMERS, METHODS OF MAKING, AND MEDICAL DEVICES

(71) Applicant: Medtronic, Inc., Minneapolis, MN (US)

(72) Inventors: Kimberly A. Chaffin, Woodbury, MN (US); Xiangji Chen, Plymouth, MN (US); Matthew Jolly, Minneapolis, MN (US); SuPing Lyu, Maple Grove, MN (US); Peter L. Thor, Arden Hills, MN (US); Darrel F. Untereker, Cedar, MN (US); Zhaoxu Wang, New Brighton, MN (US)

(73) Assignee: Medtronic, Inc., Minneapolis, MN (US)

(*) Notice: Subject to any disclaimer, the term of this patent is extended or adjusted under 35 U.S.C. 154(b) by 0 days.

This patent is subject to a terminal disclaimer.

(21) Appl. No.: 17/112,344

(22) Filed: Dec. 4, 2020

(65) Prior Publication Data

US 2021/0115182 A1   Apr. 22, 2021

Related U.S. Application Data

(63) Continuation of application No. 16/359,079, filed on Mar. 20, 2019, now Pat. No. 10,882,945.

(60) Provisional application No. 62/648,098, filed on Mar. 26, 2018.

(51) Int. Cl.

| | |
|---|---|
| *C08G 18/62* | (2006.01) |
| *C08G 18/76* | (2006.01) |
| *C08G 18/32* | (2006.01) |
| *A61N 1/05* | (2006.01) |
| *C08G 18/10* | (2006.01) |
| *A61L 31/16* | (2006.01) |
| *A61L 31/06* | (2006.01) |
| *C08G 18/65* | (2006.01) |
| *A61B 5/145* | (2006.01) |
| *A61B 5/00* | (2006.01) |
| *A61N 1/36* | (2006.01) |
| *A61N 1/362* | (2006.01) |

(52) U.S. Cl.
CPC ...... *C08G 18/6204* (2013.01); *A61B 5/14503* (2013.01); *A61B 5/6847* (2013.01); *A61L 31/06* (2013.01); *A61L 31/16* (2013.01); *A61N 1/05* (2013.01); *A61N 1/056* (2013.01); *C08G 18/10* (2013.01); *C08G 18/3206* (2013.01); *C08G 18/6511* (2013.01); *C08G 18/7671* (2013.01); *A61B 2562/12* (2013.01); *A61N 1/362* (2013.01); *A61N 1/3605* (2013.01); *A61N 1/36062* (2017.08); *A61N 1/36071* (2013.01)

(58) Field of Classification Search
CPC ........ A61N 1/05; A61N 1/056; A61N 1/3605; A61N 1/36062; A61N 1/36071; A61N 1/362; C08G 18/10; C08G 18/3206; C08G 18/6204; C08G 18/6511; C08G 18/7671; A61B 5/14503; A61B 1/6847; A61B 2562/12; A61L 31/06; A61L 31/16
See application file for complete search history.

(56) References Cited

U.S. PATENT DOCUMENTS

| | | | |
|---|---|---|---|
| 4,316,973 A | 2/1982 | Kennedy | |
| 4,321,343 A * | 3/1982 | Rooney | C08G 18/6204 525/131 |
| 4,342,849 A | 8/1982 | Kennedy | |
| 4,497,326 A | 2/1985 | Curry | |
| 4,947,866 A | 8/1990 | Lessar et al. | |
| 5,058,584 A | 10/1991 | Bourgeois | |
| 5,081,203 A | 1/1992 | Pedain et al. | |
| 5,282,468 A | 2/1994 | Klepinski | |
| 5,303,704 A | 4/1994 | Molacek et al. | |
| 5,443,492 A | 8/1995 | Stokes et al. | |
| 5,589,563 A | 12/1996 | Ward et al. | |
| 5,628,778 A | 5/1997 | Kruse et al. | |
| 5,865,843 A | 2/1999 | Baudino | |
| 5,912,302 A | 6/1999 | Gadkari et al. | |
| 5,922,014 A | 7/1999 | Warman et al. | |
| 5,962,620 A | 10/1999 | Reich et al. | |
| 5,999,858 A | 12/1999 | Sommer et al. | |

(Continued)

FOREIGN PATENT DOCUMENTS

| | | |
|---|---|---|
| CA | 1082387 | 7/1980 |
| CN | 1221430 | 6/1999 |

(Continued)

OTHER PUBLICATIONS

Albarran, Alejandra Alvarez, et al., Synthesis of Functionalized Polyisobutylenes Using the Propylene Epoxide/WiCl4 Initiating System, Polymer Chemistry, 2014, pp. 4710-4714, vol. 5, Issue 16.

(Continued)

*Primary Examiner* — Christopher M Rodd

(74) *Attorney, Agent, or Firm* — Mueting Raasch Group

(57) ABSTRACT

A modified polyisobutylene-based polymer, method of making, and a medical device that includes such polymer, wherein the modified polyisobutylene-based polymer includes urethane, urea, or urethane-urea groups, hard segments, and soft segments, wherein the soft segments comprise phenoxy-containing polyisobutylene residues, and the hard segments include diisocyanate residues and optionally chain extender residues.

18 Claims, 2 Drawing Sheets

(56) References Cited

U.S. PATENT DOCUMENTS

| | | | |
|---|---|---|---|
| 6,149,678 | A | 11/2000 | Didomenico et al. |
| 6,785,576 | B2 | 8/2004 | Verness |
| 7,860,580 | B2 | 12/2010 | Falk et al. |
| 7,884,171 | B2 | 2/2011 | Ward et al. |
| 8,155,759 | B2 | 4/2012 | Pinchuk |
| 8,324,290 | B2 | 12/2012 | Desai et al. |
| 8,374,704 | B2 | 2/2013 | Desai et al. |
| 8,497,023 | B2 | 7/2013 | Myung et al. |
| 8,501,831 | B2 | 8/2013 | Desai et al. |
| 8,529,934 | B2 | 9/2013 | Desai et al. |
| 8,552,118 | B2 | 10/2013 | Kennedy et al. |
| 8,644,952 | B2 | 2/2014 | Desai et al. |
| 8,660,663 | B2 | 2/2014 | Wolf et al. |
| 8,676,344 | B2 | 3/2014 | Desai et al. |
| 8,903,507 | B2 | 12/2014 | Desai et al. |
| 8,911,760 | B2 | 12/2014 | Boden et al. |
| 8,911,769 | B2 | 12/2014 | Spencer et al. |
| 8,927,660 | B2 | 1/2015 | Desai et al. |
| 8,942,723 | B2 | 1/2015 | Kim et al. |
| 8,942,823 | B2 | 1/2015 | Desai et al. |
| 9,359,465 | B2 | 6/2016 | Kennedy et al. |
| 9,574,043 | B2 | 2/2017 | Faust et al. |
| 9,587,067 | B2 | 3/2017 | Kennedy et al. |
| 9,631,042 | B2 | 4/2017 | Boden et al. |
| 9,650,449 | B2 | 5/2017 | Storey et al. |
| 10,882,945 | B2 | 1/2021 | Chaffin et al. |
| 2001/0053933 | A1 | 12/2001 | Phaneuf et al. |
| 2008/0275429 | A1 | 11/2008 | Sage |
| 2009/0326077 | A1 | 12/2009 | Desai et al. |
| 2010/0179298 | A1* | 7/2010 | Faust ................ C08G 18/32 528/75 |
| 2010/0184918 | A1 | 7/2010 | Storey et al. |
| 2011/0045030 | A1 | 2/2011 | Desai et al. |
| 2011/0054580 | A1 | 3/2011 | Desai et al. |
| 2011/0054581 | A1 | 3/2011 | Desai et al. |
| 2011/0213084 | A1* | 9/2011 | Kennedy ............ C08G 18/10 525/131 |
| 2013/0131765 | A1 | 5/2013 | Polkinghorne et al. |
| 2013/0131767 | A1 | 5/2013 | Desai et al. |
| 2013/0331537 | A1 | 12/2013 | Gray, Jr. et al. |
| 2013/0331538 | A1 | 12/2013 | Kennedy et al. |
| 2014/0005349 | A1 | 1/2014 | Kennedy et al. |
| 2014/0084963 | A1 | 3/2014 | Moore et al. |
| 2014/0088218 | A1 | 3/2014 | Desai et al. |
| 2014/0194963 | A1 | 7/2014 | Desai et al. |
| 2015/0025608 | A1 | 1/2015 | Delaney, Jr. et al. |
| 2015/0079406 | A1 | 3/2015 | Tennebroek et al. |
| 2015/0203622 | A1 | 7/2015 | Boden et al. |
| 2015/0274876 | A1 | 10/2015 | Faust et al. |
| 2015/0284501 | A1 | 10/2015 | Wamprecht et al. |
| 2016/0008607 | A1 | 1/2016 | Kane et al. |
| 2016/0083487 | A1 | 3/2016 | Burdzy et al. |
| 2016/0122464 | A1 | 5/2016 | Seppala et al. |
| 2016/0311983 | A1 | 10/2016 | Delaney, Jr. et al. |
| 2017/0106124 | A1 | 4/2017 | Delaney, Jr. et al. |
| 2017/0174845 | A1 | 6/2017 | Delaney, Jr. et al. |
| 2018/0016380 | A1 | 1/2018 | Coury et al. |
| 2021/0115182 | A1 | 4/2021 | Chaffin et al. |

FOREIGN PATENT DOCUMENTS

| | | |
|---|---|---|
| CN | 102131530 | 7/2011 |
| CN | 102333802 | 1/2012 |
| CN | 103554897 | 2/2014 |
| CN | 104220474 | 12/2014 |
| CN | 104704017 | 6/2015 |
| CN | 105764937 | 7/2016 |
| WO | 2016/098073 | 6/2016 |
| WO | 2018/157342 | 9/2018 |
| WO | 2019/190905 | 10/2019 |

OTHER PUBLICATIONS

Chaffin, Kimberly Al., et al., Abrasion and Fatigue Resistance of PDMS Containing Multiblock Polyurethanes After ccelerated Water Exposure at Elevated Temperature, Biomaterials, 2013, pp. 8030-8041, vol. 34.
Chaffin, Kimberly A., et al., Influence of Water on the Structure and Properties of PDMS-Containing Multiblock Polyurethanes, Macromolecules, 2012, pp. 9110-9120, vol. 45.
Frautschi, Jack R., et al., Degradation of Polyurethanes In Vitro and In Vivo: Comparison of Different Models, Colloids and Surfaces B Biointerfaces, 1, 1993, pp. 305-313.
Gunatillake, Pathiraja et al., Developments in Design and Synthesis of Biostable Polyurethanes, Biomedical pplications of Polyurethanes, 2001, pp. 160-174, Chapter 6.
Ivan, Bela et al., Living Carbocationic Polymerization. III. One-Pot Synthesis of Allyl-Terminated Linear and Tri-Arm Star Polyisobutylenes, and Epoxy- and Hydroxy-Telechelics Therefrom, Journal of Polymer Science: Part A: Polymer Chemistry, 1990, pp. 89-104, vol. 28.
Juewraijka, Suresh K., et al., Polyisobutylene-Based Segmented Polyureas. I. Synthesis of Hydrolytically and Oxidatively Stable Polyureas, Journal of Polymer Science: Part A: Polymer Chemistry, 2009, pp. 38-48, vol. 47.
Kali, Gergely, et al., Themally Responsive Amphiphilic Conetworks and Gels Based on Poly(N-isopropylacrylamide) 1:tnd Polyisobutylene, Macromolecules, 2013, pp. 5337-5344, vol. 46.
Kang, Jungmee, et al., Polyisobutylene-Based Polyurethanes with Unprecedented Properties and How They Came bout. Polymer Chemistry, 2011, pp. 3891-3904, vol. 49.
Kennedy, Joseph P., Synthesis, Characterization and Properties of Polyisobutylene-Based Polyurethanes, Journal o Elastomers and Plastics, Jan. 1985, pp. 82-88, vol. 17.
Kennedy, Joseph P., Novel Polyurethanes and Polyureas for Biomaterials, Research at The University of Akron, 017.
Lamba, Nina M.K., et al., Table of Contents from Polyurethanes in Biomedical Applications, CRC Press Book, 1st Edition, Nov. 25, 1997, 288 pages, ISBN 9780849345173.
Mitzner, E., Modification of Segmented Poly(etherurethanes) by Incorporation of Poly(isobutylene) Glycol, J.M.S.—PureAppl. Chem., 1997, pp. 165-178, A34(1).
Morgan, David L., et al., End-Quenching of TiCl4-Catalyzed Quasiliving Polyisobutylene with Alkoxybenzenes for Direct Chain End Functionalization, Macromolecules, 2010, pp. 8724-8740, vol. 43.
Ojha, Umaprasana, et al., Synthesis and Characterization of Novel Biostable Polyisobutylene Based Thermoplastic Polyurethanes, Polymer, 2009, pp. 3448-3457, vol. 50.
Schubert, Mark A., et al., Role of Oxygen in Biodegradation of Poly(etherurethaneurea) Elastomers, Journal of Biomedical Materials Research, 1997, pp. 519-530, vol. 34.
Speckhard, Ta, et al., Properties of Polyisobutylene Polyurethane Block Copolymers: 2. Macroglycols Produced DY the 'Infer' Technique, Polymer, Jan. 1985, pp. 55-69, vol. 26.
Speckhard, Ta, et al., Properties of Polyisobutylene Polyurethane Block Copolymers: 3. Hard Segments Based on J,4'-dicyclohexylmethane diisocyanate (H12MDI) and Butane Dial, Polymer, Jan. 1985, pp. 70-78, vol. 26.
Tang, Y.W., et al., Enzyme-Induced Biodegration of Polycarobonates-Polyurethanes: Dependence on Hard-Segment Chemistry, Journal of Biomedical Materials Research, Apr. 26, 2001, pp. 597-611.
Wiggins, Michael J., et al., Biodegradation of Polyether Polyurethane Inner Insulation in Bipolar Pacemaker Leads, ournal of Biomedical Materials Research, May 1, 2001, vol. 58(3), pp. 302-307.
Yoon, Sung Chui, et al., Surface and Bulk Structure of Segmented Poly(ehterurethanes) with Perfluoro Chain f:: xtenders: 5. Incorporation of Poly(dimethylsiloxane) and Polyisobutylene Macroglycols, Macromolecules, 1994, pp. 1548-1554, vol. 27.
(PCT/US2019/023570) PCT Notification of Transmittal of the International Search Report and the Written Opinion of the International Searching Authority, dated Jun. 3, 2019, 10 pages.
International Search Report and Written Opinion dated Jun. 3, 2019 for PCT/US2019/023540; 8 pages.

(56) References Cited

OTHER PUBLICATIONS

Mishra et al., "Long-term in vitro hydrolytic stability of thermoplastic polyurethanes" J Biomed Mater Res A, Dec. 2015;103(12):3798-806. Epub Jul. 1, 2015.

* cited by examiner

MODIFIED POLYISOBUTYLENE-BASED POLYMERS, METHODS OF MAKING, AND MEDICAL DEVICES

RELATED APPLICATIONS

This application is a continuation of U.S. patent application Ser. No. 16/359,079, filed Mar. 20, 2019, which claims the benefit of the filing date of U.S. Provisional Application No. 62/648,098, filed Mar. 26, 2018, the content of which are incorporated by reference in their entireties.

BACKGROUND

There is a need for soft flexible polymers and constructs thereof with improved biostability for implantable medical devices, such as electrical lead insulation, drug infusion catheters, artificial polymer discs, etc. Widely adopted soft 80A durometer polyether-polyurethanes (e.g., those available under the tradenames PELLETHANE, ELASTHANE, TECOTHANE) have desirable hydrolytic stability, mechanical properties, and processing characteristics that have led to their adoption in the implantable medical device industry. These materials are susceptible to oxidation, however, which is generally thought to occur from oxygen-based free radicals, originating from macrophages or foreign body giant cells or catalyzed by metal ions. These radicals can extract a hydrogen atom from the methylene group adjacent to the ether functionality in the polyether soft segment, resulting in chain scission. The oxidative processes observed in vivo with polyurethanes are commonly referred to as Environment Stress Cracking (ESC) and Metal Ion Oxidation (MIO).

Since the observations back in the early 1980's of oxidative degradation of soft polyether-polyurethanes, the implantable medical device industry has continuously explored soft 80A polyurethanes with improved oxidative stability, such as poly(dimethyl siloxane)-polyurethanes or PDMS-polyurethanes (e.g., those available under the trade names ELAST-EON and PURSIL) and polycarbonate-polyurethanes (e.g., that available under the tradename BIONATE). Despite their well-documented improved oxidative stability, however, these materials have not been widely adopted for various reasons.

Polycarbonate-polyurethanes show better oxidation stability compared to polyether-polyurethanes; however, they are still susceptible to oxidation to a certain degree. Also, the carbonate groups in the soft segment is considered hydrolysable under certain condition. PDMS-polyurethanes have recently been proven to be susceptible to hydrolysis resulting in decreasing mechanical strength. It should be noted that hydrolysis, unlike oxidation, typically occurs throughout the polymer as water can readily diffuse into the bulk. Consequently, bulk mechanical properties are affected by hydrolysis, whereas cell-mediated oxidation takes place primarily at the surface.

Another obstacle is the commercial supply of PIB-based polyurethane. PIB-diol is difficult to make. The conventional route for making PIB diol includes two reactions: 1) polymerizing isobutylene and capping the polymer chain ends with allyl functionalities; and 2) converting these allyl functionalities on the polymer chains into hydroxyl functionalities. This route is time consuming and costly considering each step requires a whole process from reaction set-up to product purifying. PIB-diol is also expensive to make and there are many expensive chemicals needed in the process. One of them is the initiator. There is also a conventional notion that the initiator for polymerizing isobutylene must contain certain aromatic structures to ensure efficient initiation and therefore good product qualities. Examples of these aromatic initiator are 5-tert-butyl-1,3-bis(1-methoxy-1-methylethyl)-benzene (or "hindered dicumyl ether" or "HDCE") or 1,3-bis(1-chloro-1-methylethyl)-5-(1-dimethylethyl)benzene (or, alternatively, known as 1,3-bis(1-chloro-1-methylethyl)-5-tert-butylbenzene or "hindered dicumyl chloride" or "HDCC"). These aromatic initiators, however, are not commercially available and are costly to make.

In order to bring PIB diol-based polyurethanes into medical device applications, there is a need to reduce the cost and ease the process of making PIB-diol, hence PIB-based polyurethane.

SUMMARY

The present disclosure provides a modified polyisobutylene-based polymer and a medical device that includes such polymer.

In one embodiment, a modified polyisobutylene-based polymer is provided that includes urethane, urea, or urethane-urea groups, hard segments, and soft segments, wherein the soft segments comprise phenoxy-containing polyisobutylene residues, and the hard segments include diisocyanate residues and optionally chain extender residues.

Methods of making such polymers are also provided.

In another embodiment, a medical device is provided that includes a polymeric region including the modified polyisobutylene-based polymer described herein. Such medical devices include, for example, an implantable electrical lead, an implantable electrical pulse generator, or an implantable mechanical device.

Polymers of the present disclosure are elastomers. An "elastomer" is a polymer that is capable of being stretched to approximately twice its original length and retracting to approximately its original length upon release. Polymers of the present disclosure can be made of two or more different monomers. They can be random, alternating, block, star-shaped block, segmented copolymers, or combinations thereof. Preferably, the polymers are segmented copolymers (i.e., containing a multiplicity of both hard and soft domains or segments on any polymer chain) and are comprised substantially of alternating relatively soft segments and relatively hard segments.

As used herein, a "hard" segment is one that is crystalline at use temperature, or amorphous with a glass transition temperature above use temperature, or when in the water saturated state at body temperature, a hard segment has a Tg of about 30° C. (below body temperature, but above that of the soft segments, which are typically −100° C. to −30° C.), and a "soft" segment is one that is amorphous with a glass transition temperature below use temperature (i.e., rubbery). A crystalline or glassy moiety or hard segment is one that adds considerable strength and higher modulus to the polymer. Similarly, a rubbery moiety or soft segment is one that adds flexibility and lower modulus, but may add strength particularly if it undergoes strain crystallization, for example. The random or alternating soft and hard segments are linked by urethane groups, urea groups, or urethane-urea groups, and the polymers may be terminated by hydroxyl, amine, and/or isocyanate groups or surface modified end groups.

Herein, "phenoxy-containing polyisobutylene residues" mean that there are groups in such residues that have an oxygen atom bonded to a phenyl ring.

As used herein, "alkyl" refers to a monovalent group that is a radical of an alkane and includes straight-chain, branched, cyclic, and bicyclic alkyl groups, and combinations thereof, including both unsubstituted and substituted alkyl groups. Unless otherwise indicated, the alkyl groups typically contain from 1 to 16 carbon atoms. In some embodiments, the alkyl groups contain 1 to 10 carbon atoms, 1 to 6 carbon atoms, 1 to 4 carbon atoms, or 1 to 3 carbon atoms. In some embodiments, the cycloalkyl groups contain 3 to 16 carbon atoms, 3 to 10 carbon atoms, or 3 to 6 carbon atoms. Examples of "alkyl" groups include, but are not limited to, methyl, ethyl, n-propyl, n-butyl, n-pentyl, isobutyl, t-butyl, isopropyl, n-octyl, n-heptyl, ethylhexyl, cyclopentyl, cyclohexyl, cycloheptyl, adamantyl, norbornyl, and the like.

As used herein, "alkenyl" refers to a monovalent group that is a radical of an alkene and includes straight-chain, branched, cyclic, and bicyclic alkenyl groups, and combinations thereof, including both unsubstituted and substituted alkenyl groups. Unless otherwise indicated, the alkenyl groups typically contain from 2 to 16 carbon atoms. In some embodiments, the alkenyl groups contain 2 to 10 carbon atoms, 2 to 6 carbon atoms, or 2 to 4 carbon atoms. In some embodiments, the cycloalkenyl groups contain 3 to 16 carbon atoms, 3 to 10 carbon atoms, or 3 to 6 carbon atoms. Examples of "alkenyl" groups include, but are not limited to, ethenyl, n-propenyl, n-butenyl, n-pentenyl, isobutenyl, t-butenyl, cyclohexenyl, and the like.

As used herein, "alkynyl" refers to a monovalent group that is a radical of an alkyne and includes straight-chain, branched, cyclic, and bicyclic alkynyl groups, and combinations thereof, including both unsubstituted and substituted alkynyl groups. Unless otherwise indicated, the alkynyl groups typically contain from 2 to 16 carbon atoms. In some embodiments, the alkynyl groups contain 2 to 10 carbon atoms, 2 to 6 carbon atoms, or 2 to 4 carbon atoms. In some embodiments, the alkynyl groups contain 3 to 16 carbon atoms, 3 to 10 carbon atoms, or 3 to 6 carbon atoms. Examples of "alkynyl" groups include, but are not limited to, ethynyl, n-propynyl, n-butynyl, n-pentynyl, isobutynyl, t-butynyl, cyclohexynyl, and the like.

The term "aryl" refers to a monovalent group that is aromatic and, optionally, carbocyclic. The aryl has at least one aromatic ring. Any additional rings can be unsaturated, partially saturated, saturated, or aromatic. Optionally, the aromatic ring can have one or more additional carbocyclic rings that are fused to the aromatic ring. Unless otherwise indicated, the aryl groups typically contain from 6 to 18 carbon atoms. In some embodiments, the aryl groups contain 6 to 16 carbon atoms, 6 to 12 carbon atoms, or 6 to 10 carbon atoms. Examples of an aryl group include phenyl, naphthyl, biphenyl, phenanthryl, and anthracyl.

A "medical device" may be defined as a device that has surfaces that contact blood or other bodily fluids in the course of their operation. This can include, for example, extracorporeal devices for use in surgery, such as blood oxygenators, blood pumps, blood sensors, tubing used to carry blood, and the like, which contact blood which is then returned to the patient. This can also include endoprostheses implanted in blood contact in a human or animal body such as vascular grafts, stents, stent grafts, medical electrical leads, indwelling catheters, heart valves, and the like, that are implanted in blood vessels or in the heart. This can also include devices for temporary intravascular use such as catheters, guide wires, balloons, and the like, which are inserted into the blood vessels or the heart for purposes of monitoring or repair. Thus, a medical device may be an implantable device or an insertable device.

Herein, the term "comprises" and variations thereof do not have a limiting meaning where these terms appear in the description and claims. Such terms will be understood to imply the inclusion of a stated step or element or group of steps or elements but not the exclusion of any other step or element or group of steps or elements. By "consisting of" is meant including, and limited to, whatever follows the phrase "consisting of" Thus, the phrase "consisting of" indicates that the listed elements are required or mandatory, and that no other elements may be present. By "consisting essentially of" is meant including any elements listed after the phrase, and limited to other elements that do not interfere with or contribute to the activity or action specified in the disclosure for the listed elements. Thus, the phrase "consisting essentially of" indicates that the listed elements are required or mandatory, but that other elements are optional and may or may not be present depending upon whether they materially affect the activity or action of the listed elements. Any of the elements or combinations of elements that are recited in this specification in open-ended language (e.g., comprise and derivatives thereof), are considered to additionally be recited in closed-ended language (e.g., consist and derivatives thereof) and in partially closed-ended language (e.g., consist essentially, and derivatives thereof).

The words "preferred" and "preferably" refer to embodiments of the disclosure that may afford certain benefits, under certain circumstances. However, other claims may also be preferred, under the same or other circumstances. Furthermore, the recitation of one or more preferred claims does not imply that other claims are not useful, and is not intended to exclude other claims from the scope of the disclosure.

In this application, terms such as "a," "an," and "the" are not intended to refer to only a singular entity, but include the general class of which a specific example may be used for illustration. The terms "a," "an," and "the" are used interchangeably with the term "at least one." The phrases "at least one of" and "comprises at least one of" followed by a list refers to any one of the items in the list and any combination of two or more items in the list.

As used herein, the term "or" is generally employed in its usual sense including "and/or" unless the content clearly dictates otherwise.

The term "and/or" means one or all of the listed elements or a combination of any two or more of the listed elements.

Also herein, all numbers are assumed to be modified by the term "about" and in certain embodiments, preferably, by the term "exactly." As used herein in connection with a measured quantity, the term "about" refers to that variation in the measured quantity as would be expected by the skilled artisan making the measurement and exercising a level of care commensurate with the objective of the measurement and the precision of the measuring equipment used. Herein, "up to" a number (e.g., up to 50) includes the number (e.g., 50).

Also herein, the recitations of numerical ranges by endpoints include all numbers subsumed within that range as well as the endpoints (e.g., 1 to 5 includes 1, 1.5, 2, 2.75, 3, 3.80, 4, 5, etc.).

As used herein, the terms "ambient temperature" or "room temperature" refer to a temperature of 20° C. to 25° C. or 22° C. to 25° C.

The term "in the range" or "within a range" (and similar statements) includes the endpoints of the stated range.

Groupings of alternative elements or embodiments disclosed herein are not to be construed as limitations. Each group member may be referred to and claimed individually or in any combination with other members of the group or other elements found therein. It is anticipated that one or more members of a group may be included in, or deleted from, a group for reasons of convenience and/or patentability. When any such inclusion or deletion occurs, the specification is herein deemed to contain the group as modified thus fulfilling the written description of all Markush groups used in the appended claims.

When a group is present more than once in a formula described herein, each group is "independently" selected, whether specifically stated or not. For example, when more than one R group is present in a formula, each R group is independently selected.

Reference throughout this specification to "one embodiment," "an embodiment," "certain embodiments," or "some embodiments," etc., means that a particular feature, configuration, composition, or characteristic described in connection with the embodiment is included in at least one embodiment of the invention. Thus, the appearances of such phrases in various places throughout this specification are not necessarily referring to the same embodiment of the invention. Furthermore, the particular features, configurations, compositions, or characteristics may be combined in any suitable manner in one or more embodiments.

The above summary of the present disclosure is not intended to describe each disclosed embodiment or every implementation of the present invention. The description that follows more particularly exemplifies illustrative embodiments. In several places throughout the application, guidance is provided through lists of examples, which examples may be used in various combinations. In each instance, the recited list serves only as a representative group and should not be interpreted as an exclusive list. Thus, the scope of the present disclosure should not be limited to the specific illustrative structures described herein, but rather extends at least to the structures described by the language of the claims, and the equivalents of those structures. Any of the elements that are positively recited in this specification as alternatives may be explicitly included in the claims or excluded from the claims, in any combination as desired. Although various theories and possible mechanisms may have been discussed herein, in no event should such discussions serve to limit the claimable subject matter.

DETAILED DESCRIPTION OF ILLUSTRATIVE EMBODIMENTS

Figure 1:
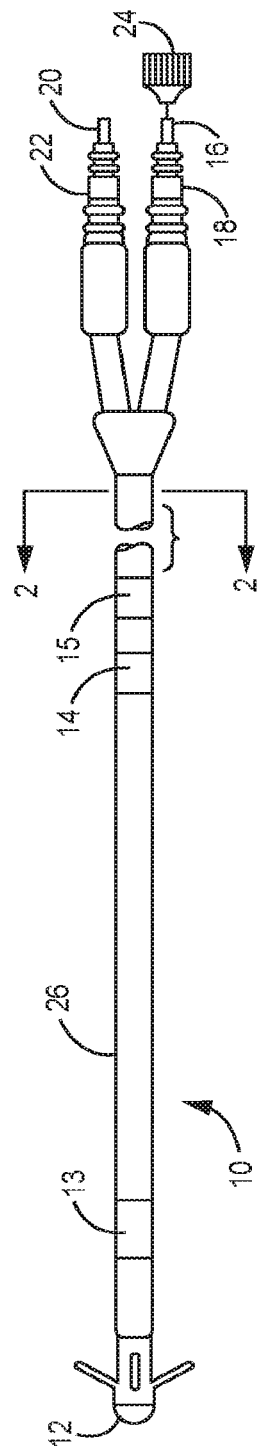
FIG. 1 is a diagram of a lead which incorporates a polymer of the present disclosure.

This disclosure provides a modified polyisobutylene-based polymer and a medical device that includes such polymer.

In one embodiment, a modified polyisobutylene-based polymer is provided that includes urethane, urea, or urethane-urea groups, hard segments, and soft segments, wherein the soft segments include phenoxy-containing polyisobutylene residues, and the hard segments include diisocyanate residues and optionally chain extender residues. In certain embodiments, a modified polyisobutylene-based polymer of the present disclosure includes urethane groups, and in certain embodiments, no urea groups. Such polymers are elastomers.

The use of phenoxy-containing polyisobutylene residues as soft segments results in a polymer having sufficient mechanical properties, particularly tear strength, and chemical stability compared to the similar polymers with other polyisobutylene residues and without the phenoxy-containing polyisobutylene residues.

In certain embodiments, a modified polyisobutylene-based polymer of the present disclosure has a weight average molecular weight of at least 10,000 Daltons, as determined by gel permeation chromatography with multiangle laser light scattering detection. In certain embodiments, a modified polyisobutylene-based polymer of the present disclosure has a weight average molecular weight of up to 2,000,000 Daltons, or up to 1,000,000 Daltons, as determined by gel permeation chromatography with multiangle laser light scattering detection. In certain embodiments, a modified polyisobutylene-based polymer of the present disclosure has a weight average molecular weight of 10,000 Daltons to 2,000,000 Daltons, or 10,000 Daltons to 1,000,000 Daltons, as determined by gel permeation chromatography with multiangle laser light scattering detection.

A polyurethane includes linkages of the following structure:

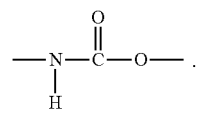

Such polymers can be made using conventional techniques. Typically, polyurethanes are made by a process in which one or more polyfunctional isocyanates (e.g., diisocyanates, including both aliphatic and aromatic diisocyanates) is reacted with one or more polyols (e.g., diols) to form a prepolymer. The resulting prepolymer can be further reacted with a chain extender, such as a diol.

A polyurea includes linkages of the following structure:

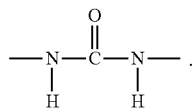

Such polymers can be made using conventional techniques. Typically, polyureas are made by a process in which one or more polyfunctional isocyanates (e.g., diisocyanates, including both aliphatic and aromatic diisocyanates) is reacted with one or more polyamines (e.g., diamines) to form a prepolymer. The resulting prepolymer can be further reacted with a chain extender, such as a diol.

A polyurethane-urea includes both of the above-described linkages. Such polymers can be made using conventional techniques. Typically, polyurethane-ureas are made by a process in which one or more polyfunctional isocyanates (e.g., diisocyanates, including both aliphatic and aromatic diisocyanates) is reacted with one or more polyamines (e.g., diamines) and one or more polyols (e.g., diols) to form a prepolymer. The resulting prepolymer can be further reacted with a chain extender, such as a diol.

In certain embodiments, the present disclosure provides a method of making a modified polyisobutylene-based polymer that includes phenoxy-containing polyisobutylene residues as described herein, wherein the method includes combining a diisocyanate, an optional chain extender, a phenoxy-containing polyisobutylene diol, damine, or combination thereof, and an optional additional soft segment-containing diol, diamine, or combination thereof under conditions effective to form the modified polyisobutylene-based polymer. Such conditions may include a conventional prepolymer technique using conventional temperatures, pressures, etc.

Soft Segments

Soft segments of the polymers of the present disclosure include phenoxy-containing polyisobutylene residues. In certain embodiments, soft segments of the polymers of the present disclosure consist essentially of phenoxy-containing polyisobutylene residues, wherein there may be small amounts of other soft segment residues but only minor amounts that do not change the properties of the polymer. In certain embodiments, soft segments of the polymers of the present disclosure consist of phenoxy-containing polyisobutylene residues, wherein there no other soft segment residues.

In certain embodiments, soft segments may also include additional residues. In certain embodiments, the additional soft segment residues are selected from poly(ether-carbonate) residues, polybutadiene residues, hydrogenated polybutadiene residues, polycarbonate residues, polyether residues, polyester residues, polysiloxane residues, and combinations thereof, which may be provided by diols, diamines, or combinations thereof.

In certain embodiments, the weight ratio of phenoxy-containing polyisobutylene residues to additional soft segment residues is up to 99:1, up to 95:5, or up to 90:10. In certain embodiments, the weight ratio of phenoxy-containing polyisobutylene residues to additional soft segment residues is at least 1:99, at least 50:50, or at least 80:20. In certain embodiments, the weight ratio of phenoxy-containing polyisobutylene residues to additional soft segment residues is within a range of 99:1 to 1:99, within a range of 95:5 to 50:50, or within a range of 90:10 to 80:20.

In certain embodiments, the soft segments include phenoxy-containing polyisobutylene residues. In certain embodiments, the phenoxy-containing polyisobutylene residues are derived from a phenoxy-containing polyisobutylene diol, a phenoxy-containing polyisobutylene diamine, or a combination thereof. In certain embodiments, the phenoxy-containing polyisobutylene residues are derived from one or more phenoxy-containing polyisobutylene diols.

In certain embodiments, the phenoxy-containing polyisobutylene residues include initiator residues and phenoxy-containing polyisobutylene residues.

In certain embodiments, the phenoxy-containing polyisobutylene residues are derived from a phenoxy-containing polyisobutylene compound of the following formula:

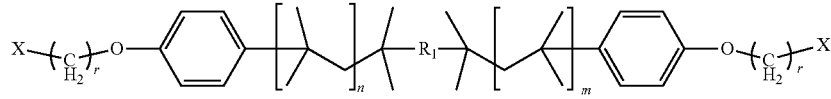

wherein $R_1$ is an initiator residue, each X is independently —OH, —$NH_2$, or —$NHR_2$, each r is independently 1 to 20, n=1-500, and m=1-500. Each of $R_2$ is selected from a (C1-C16)alkyl, a (C3-C16)cycloalkyl, a (C2-C16)alkenyl, a (C3-C16)cycloalkenyl, a (C2-C16)alkynyl, a (C3-C16)cycloalkynyl, or a (C6-C18)aryl.

In certain embodiments, the phenoxy-containing polyisobutylene residues are derived from a phenoxy-containing polyisobutylene diol of the following formula:

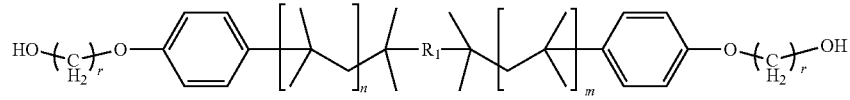

wherein R₁ is an initiator residue, each r is independently 1 to 20, n=1-500, and m=1-500.

Such initiator residues may include aromatic residues, aliphatic residues, or combinations thereof. Examples of initiators include 5-tert-1,3-bis(1-methoxy-1-methylethyl)-benzene (or "hindered dicumyl ether" or "HDCE"), 1,3-bis(1-chloro-1-methylethyl)-5-(1-dimethylethyl)benzene (or, alternatively, known as 1,3-bis(1-chloro-1-methylethyl)-5-tert-butylbenzene or "hindered dicumyl chloride" or "HDCC"), 2,6-dichloro-2,4,4,6-tetramethylheptane, and 2,5-dichloro-2,5-dimethylhexane.

In certain embodiments, the phenoxy-containing polyisobutylene residues are derived from a phenoxy-containing polyisobutylene diol of the following formula:

chain extender includes 1,2-ethane diol, 1,4-butanediol, 1,6-hexanediol, or combinations thereof.

In certain embodiments, the weight ratio of soft segments to hard segments in a modified polyisobutylene-based polymer of the present disclosure is up to 90:10, up to 80:20, or up to 70:30. In certain embodiments, the weight ratio of soft segments to hard segments in a modified polyisobutylene-based polymer of the present disclosure is at least 10:90, at least 30:70, or at least 40:60. In certain embodiments, the weight ratio of soft segments to hard segments in a modified polyisobutylene-based polymer of the present disclosure is within a range of 90:10 to 10:90, within a range of 80:20 to 30:70, or within a range of 70:30 to 40:60.

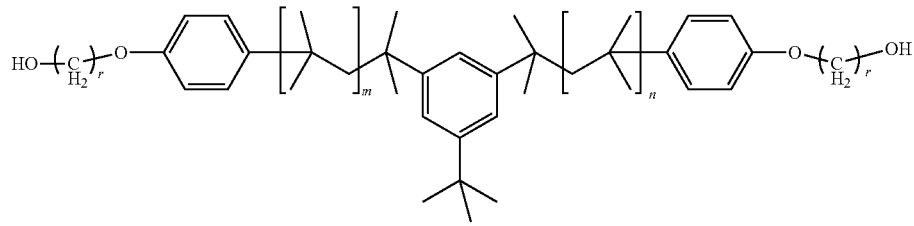

wherein each r (independently)=1-20, n=1-500, and m=1-500.

Such PIB-diols can be made with a one-step synthetic route (combining polymerizing isobutylene and installing primary hydroxyl group in one step). This PM-diol can be used to make a phenoxy-containing polyisobutylene polyurethane having sufficient mechanical properties and chemical stability suitable for use in medical devices.

Even though these initiators have been hypothesized to be less efficient at initiating cationic polymerization than more expensive initiators, the final PIB-diol can be produced using these initiators, wherein the PIB-diol has a functionality sufficiently close to 2.0 such that this PIB-diol can be used to make a modified polyisobutylene polyurethane having sufficient mechanical properties and chemical stability suitable for use in medical devices. This will significantly reduce the cost of making such polyurethanes.

Hard Segments

A modified polyisobutylene-based polymer of the present disclosure includes hard segments including diisocyanate residues and optionally chain extender residues.

In certain embodiments, the diisocyanate residues are derived from 4,4'-methylenediphenyl diisocyanate, 4,4'-methylenebis(cyclohexyl isocyanate), toluene diisocyanate, 1,5-naphthalene diisocyanate, para-phenylene diisocyanate, 3,3'-tolidene-4,4'-diisocyanate, 3,3'-dimethyldiphenylmethane-4,4'-diisocyanate, and combinations thereof. In certain embodiments, the diisocyanate residues are derived from 4,4'-methylenediphenyl diisocyanate (MDI) to contribute to a polymer having excellent hydrolysis stability.

In certain embodiments, hard segments include chain extender residues. In certain embodiments, the chain extender residues are derived from at least one chain extender selected from an aliphatic diol, an aromatic diol, an aliphatic diamine, an aromatic diamine, and a combination thereof. In certain embodiments, the chain extender includes one or more aliphatic diols. In certain embodiments, the aliphatic diol chain extender includes one or more alpha, omega-(C1-C16)alkane diols. In certain embodiments, the Medical Devices The present disclosure also provides medical devices. Such devices include a polymeric region including the modified polyisobutylene-based polymer described herein. Such medical devices include, for example, an implantable electrical lead, an implantable electrical pulse generator, or an implantable mechanical device (e.g., ventricle assistance device, pump, and an artificial valve such as a prosthetic heart valve).

A prosthetic heart valve replaces the function of a native heart valve such that the prosthetic valve regulates the flow of blood through the heart. In one aspect, a prosthetic heart valve includes a base and a plurality of polymeric leaflets. Each leaflet has a root portion coupled to the base, and each leaflet has an edge portion substantially opposite the root portion and movable relative to the root portion to coat with a respective edge portion of at least one of the other leaflets of the plurality of leaflets.

Particularly suitable medical devices include medical leads. Medical leads are used to transmit electrical signals to and from medical devices such as pacemakers and neurostimulators, for example. The lead body is usually made from a piece of polymeric tubing having a round cross-section exterior and a round cross-section lumen. Typically, a coiled metallic electrical conductor having a round cross-section is placed in the lumen completely filling it. The tubing protects and insulates the conductor. The coiled conductor can usually receive a stylet to help position and place the lead during implantation. There are many examples of medical electrical leads, including, for example, those described in U.S. Pat. No. 6,785,576 (Verness), U.S. Pat. No. 5,303,704 (Molacek et al.), U.S. Pat. No. 5,999,858 (Sommer et al.), U.S. Pat. No. 6,149,678 (DiDomenico et al.), U.S. Pat. No. 4,947,866 (Lessar et al.), U.S. Pat. No. 5,922,014 (Warman et al.), U.S. Pat. No. 5,628,778 (Kruse et al.), U.S. Pat. No. 4,497,326 (Curry), U.S. Pat. No. 5,443,492 (Stokes et al.), and U.S. Pat. No. 7,860,580 (Falk et al.).

In certain embodiments, the medical device is an implantable electrical lead. In certain embodiments, the electrical lead is a cardiac lead or a neurostimulation lead. In certain embodiments, the implantable electrical lead includes an electrical conductor and a layer including a modified polyisobutylene-based polymer of the present disclosure disposed on the electrical conductor. In certain embodiments, the polymeric region further includes a therapeutic agent (i.e., a drug).

As an exemplary embodiment of a medical electrical lead, FIG. 1 is a diagram of a lead assembly 10, which incorporates a polymer of the present disclosure. The lead body 26 carries four electrodes including ventricular electrodes 12 and 13 and atrial electrodes 14 and 15. Within the lead body are four conductors, one coupled to each of the electrodes and extending proximally to a corresponding electrical connector. The proximal end of the lead assembly 10 has a dual in-line connector assembly including connector pin 16, coupled to electrode 12, connector ring 18, coupled to electrode 13, connector pin 20, coupled to electrode 14 and connector ring 22, coupled to electrode 15. A stylet 24 may be 25 inserted into the lead through pin 16 to stiffen it as an aid to implantation.

Lead body 26 in FIG. 1 is preferably fabricated of silicone rubber, polyurethane or other implantable polymer. In particular, lead body 26 is preferably fabricated of a polymer of the present disclosure.

Electrodes 12, 13, 14, and 15 in FIG. 1 are preferably fabricated of platinum alloy or 30 other biocompatible metal. Connectors 16, 18, 20, and 22 are preferably fabricated of stainless steel or other biocompatible metal.

As illustrated, the lead includes electrodes which may serve as means for delivery of stimulation pulses and as means for sensing physiological electrical signals. It should also be understood that a lead according to the present disclosure may also include means for sensing other physiological parameters, such as pressure, oxygen saturation, temperature, or pH. The lead may include electrodes only, other physiologic sensors only, or a combination of both.

Figure 2:
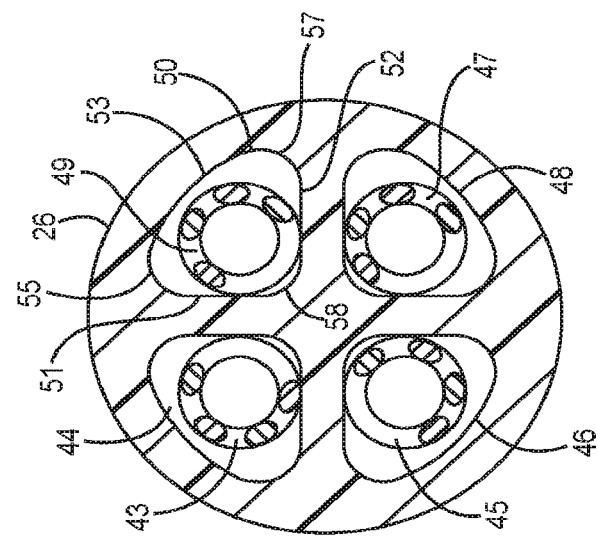
FIG. 2 is a cross-sectional view of the lead body of the lead shown in FIG. 1.

FIG. 2 is a cross-section through the lead body 26. In this view, it can be seen that lead body 26 is provided with four pie-shaped or generally triangular lumens. The first lumen 44 contains a first coiled conductor 43. The second lumen 46 contains a second coiled conductor 45. The third lumen 48 contains a third coiled conductor 47. The fourth lumen 50 contains a fourth coiled conductor 49. The conductors 43, 45, 47, and 49 are preferably fabricated of MP35N alloy or other biocompatible metal. In the drawing each coiled conductor is shown as a multi-filar coil; however, monofilar coils are useful as well.

One of the four conductors is coupled to pin 16 and also serves to receive a stylet. The lead body may employ the multi-lumen configuration illustrated over its entire length, with two of the lumens unused distal to electrodes 14 and 15. Alternatively, a transition to a lead body having a coaxial or side by side two-lumen configuration as typically used in bipolar pacing leads may occur at or distal to electrodes 14 and 15. As seen in cross section, the representative fourth lumen 50 has three walls each having a radius of curvature substantially greater than the radius of curvature of the conductor coil. These walls include two substantially planar walls 51 and 52 each extending along a radius of the body and an outer curved wall 53, extending along the outer circumference of the lead body. The walls are joined to one another along corners 55, 57, and 58 each of which have a radius of curvature substantially less than the radius of curvature of the conductor coils, as seen in this cross-section.

In certain embodiments, contact between a coil of a conductor and the inner surface of a lumen will be limited to those portions of the inner surfaces of the lumen which have a substantially greater radius of curvature than the conductor coil. Contact will thus be limited to discrete points of contact, rather than along substantial lengths of the individual coils, as would occur in prior leads employing circular coils and circular lumens of similar sizes. Contact will occur only along walls 51, 52, and 53, and not in corners 55, 57, and 59. Along the length of the lead, individual coils will contact various points on all three walls 51, 52, and 53.

The present medical electrical lead includes a polymeric material of the present disclosure as part or all of lead body 26, but theoretically this could apply to any insulator on the lead body.

Figure 3:
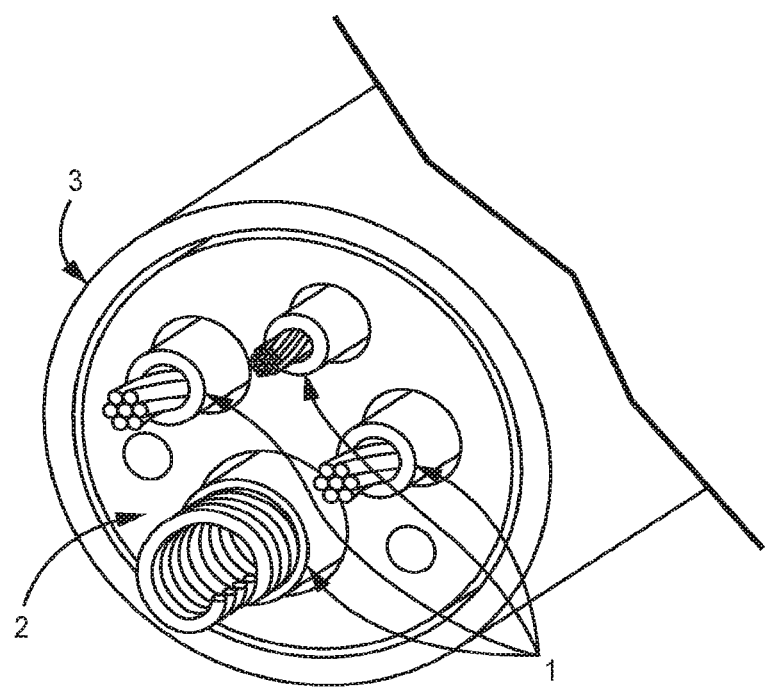
FIG. 3 is a cross-section of an exemplary lead body.

FIG. 3 is a cross-section of another exemplary lead body showing several insulation layers: a primary insulation layer 1, which encapsulates the conductors; a secondary insulation layer 2, which contains the lumens for the conductors; and a tertiary outer insulation layer 3. The polymer of this disclosure forms part or all of any of these insulation layers.

Medical, neurological leads are used for insertion into the human body, for transmission of therapeutic agents (i.e., drugs) and/or electrical signals to body organs such as the spinal cord or brain, for acute and chronic pain relief, acute and chronic treatment of disease, and the like. The leads are used in programmable, electronic, implantable devices which deliver drugs and/or electrical stimulation in programs of therapy for the benefit of mankind.

Implantable electrical devices are capable of relieving chronic, inoperable pain by interfering with the transmission of pain signals in the spinal cord and brain. Implantable drug delivery devices are capable of delivering pain relieving drugs to the same dramatic effect. Both types of devices are also capable of new therapies for treatment of a variety of diseases. An advantage of the electrical devices is that typically no drugs are necessary. With the drug delivery devices, an advantage is that drug dosages are reduced relative to other therapies because the drugs are delivered directly to desired locations of therapy, rather than in remote locations such as the blood vessels of the extremities, and without concern for bodily elimination or chemical interaction.

With the electrical devices, electrical stimulation is typically delivered from the devices to the body through wired leads, to electrodes. The electrodes are located on and exposed to the body on the distal extremity of the leads, and the leads typically extend into and along the epidural space of the spinal cord, or into the brain at surgically drilled boreholes. The leads may also be subcutaneous where necessary. As an example, leads may extend from devices implanted above the clavicles, under the skin, to a bore hole atop the skull, and thence deep into brain tissue.

With the drug delivery devices, catheters, which for purposes of this description are also considered "neurological leads," extend in similar ways. Leads in the described applications are typically smooth walled, plastic, tubular members, although variation is possible. There are many examples of medical neurological leads, including, for example, those described in U.S. Pat. No. 5,058,584 (Bourgeois), U.S. Pat. No. 5,865,843 (Baudino), U.S. Pat. Pub. No. 2008/0275429 (Sage). Medical neurological leads include, for example, paddle leads, in-line cylindrical leads, and drug delivery catheters. These leads/catheters can be placed in numerous locations. Electrode leads are used in the epidural space, within the brain itself, in the sacral root, and within blood vessels. Cuff-type electrodes, as in U.S. Pat. No. 5,282,468 (Klepinski), can be mounted around nerve bundles or fibers. Drug delivery catheters can be placed in/adjacent the spinal column or any location within the vascular system. The polymeric material of the present disclosure may be used as all or part of the lead body, as insulation, as an inner or outer layer, etc.

Figure 4:
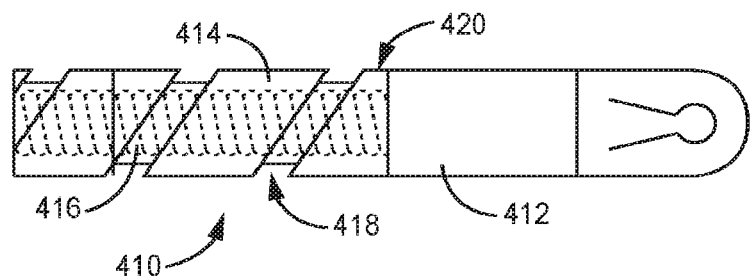
FIG. 4 is a diagram of a neurological electrical lead which incorporates a polymer of the present disclosure.
Figure 5:
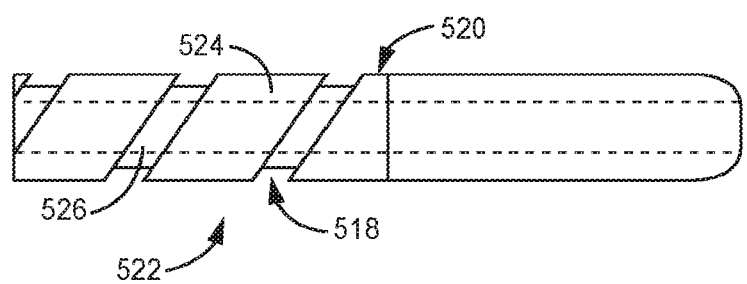
FIG. 5 is a diagram of a neurological drug delivery lead which incorporates a polymer of the present disclosure.

Referring to FIGS. 4 and 5, an exemplary lead of the disclosure includes a distal portion 10, and associated central and proximal portions not shown. As known to persons of ordinary skill in the art, if electrical, the lead may connect to an electrical signal generating device (hereafter "a signal generator"), which may or may not be implantable in whole or in part into the human body. If the lead is a drug delivery lead, the lead may connect to a drug pump, which also may or may not be implantable. In either case, the lead is intended to have at least a portion engaged in the tissue of the body. Depending on the application, the lead may engage tissue in the proximal, central, or distal portions of the lead. The lead may or may not enter the epidural space which surrounds the spinal cord, or the lead may enter the brain through the skull. Generally, the lead is substantially elongated, with the dimension of its length one hundred or more times the dimension of its width.

Again, if electrical, as in FIG. 4, the lead 410 may include one or more electrodes, such as an electrode designated 412. The electrode may be annular, surrounding the lead 30 body, or in other shape or form. If a drug delivery lead, as in FIG. 5, the lead 522 may include one or more openings for transmission of drugs from the drug pump to the body, in the place of electrodes, or in addition to electrodes.

The lead 410 or 522 is desirably, generally circular in cross-section, although variations are within contemplation. Focusing on an electrical lead of FIG. 4, for illustration, an insulating, annular, external lead sheath or body 414 surrounds an electrically transmissive internal core 416, shown in phantom. The core 416 frequently takes the form of a helically wound or coiled wire, interconnected to the distal electrode(s) and the proximal signal generator. The wire has a direction of its winding, which is right hand or left hand, clockwise or counterclockwise. As desired, although not presently contemplated, the lead may also include additional intermediate or other layers, or other components.

FIG. 4. shows an electrical lead having a helical groove 418, and associated helical land 420. FIG. 5 shows a drug delivery lead or catheter having a liquid insulating, annular, external lead sheath or body 524 surrounds a liquid transmissive internal and open core or passage 526, shown in phantom.

Embodiments

Embodiment 1 is a modified polyisobutylene-based polymer comprising (or consisting essentially of or consisting of) urethane, urea, or urethane-urea groups, hard segments, and soft segments, wherein the soft segments comprise (or consist essentially of or consist of) phenoxy-containing polyisobutylene residues, and the hard segments comprise (or consist essentially of or consist of) diisocyanate residues and optionally chain extender residues.

Embodiment 2 is the modified polyisobutylene-based polymer of embodiment 1 comprising urethane groups.

Embodiment 3 is the modified polyisobutylene-based polymer of embodiment 1 or 2 wherein the diisocyanate residues are derived from 4,4'-methylenediphenyl diisocyanate, 4,4'-methylenebis(cyclohexyl isocyanate), toluene diisocyanate, 1,5-naphthalene diisocyanate, para-phenylene diisocyanate, 3,3'-tolidene-4,4'-diisocyanate, 3,3'-dimethyl-diphenylmethane-4,4'-diisocyanate, and combinations thereof.

Embodiment 4 is the modified polyisobutylene-based polymer of any of the previous embodiments wherein the hard segments comprise chain extender residues.

Embodiment 5 is the modified polyisobutylene-based polymer of embodiment 4 wherein the chain extender residues are derived from at least one chain extender selected from an aliphatic diol, an aromatic diol, an aliphatic diamine, an aromatic diamine, and a combination thereof.

Embodiment 6 is the modified polyisobutylene-based polymer of embodiment 5 wherein the chain extender comprises an aliphatic diol.

Embodiment 7 is the modified polyisobutylene-based polymer of embodiment 6 wherein the aliphatic diol chain extender comprises an alpha, omega-(C1-C16)alkane diol.

Embodiment 8 is the modified polyisobutylene-based polymer of embodiment 7 wherein the chain extender comprises 1,2-ethane diol, 1,4-butanediol, 1,6-hexanediol, or combinations thereof.

Embodiment 9 is the modified polyisobutylene-based polymer of any of the previous embodiments wherein the soft segments further comprise additional soft segment residues.

Embodiment 10 is the modified polyisobutylene-based polymer of embodiment 9 wherein the additional soft segment residues are selected from poly(ether-carbonate) residues, polybutadiene residues, hydrogenated polybutadiene residues, polycarbonate residues, polyether residues, polyester residues, polysiloxane residues, and combinations thereof.

Embodiment 11 is the modified polyisobutylene-based polyurethane of embodiment 9 or 10 wherein the additional soft segment residues are derived from a diol, a diamine, or a combination thereof.

Embodiment 12 is the modified polyisobutylene-based polymer of any of embodiments 9 through 11 wherein the weight ratio of phenoxy-containing polyisobutylene residues to additional soft segment residues is up to 99:1 (or up to 95:5, or up to 90:10).

Embodiment 13 is the modified polyisobutylene-based polymer of any of embodiments 9 through 12 wherein the weight ratio of phenoxy-containing polyisobutylene residues to additional soft segment residues is at least 1:99 (or at least 50:50, or at least 80:20).

Embodiment 14 is the modified polyisobutylene-based polymer of embodiments 12 or 13 wherein the weight ratio of phenoxy-containing polyisobutylene residues to additional soft segment residues is within a range of 99:1 to 1:99 (or within a range of 95:5 to 50:50, or within a range of 90:10 to 80:20).

Embodiment 15 is the modified polyisobutylene-based polymer of any of the previous embodiments wherein the phenoxy-containing polyisobutylene residues are derived from a phenoxy-containing polyisobutylene diol, a phenoxy-containing polyisobutylene diamine, or a combination thereof (preferably, a diol).

Embodiment 16 is the modified polyisobutylene-based polymer of any of the previous embodiments wherein the phenoxy-containing polyisobutylene residues comprise aromatic-containing and phenoxy-containing polyisobutylene residues.

Embodiment 17 is the modified polyisobutylene-based polymer of embodiment 16 wherein the phenoxy-containing polyisobutylene residues are derived from a phenoxy-containing polyisobutylene compound of the following formula:

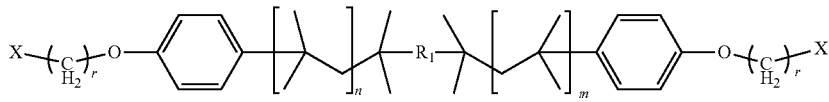

wherein $R_1$ is an initiator residue, each X is independently —OH, —NH$_2$, or —NHR$_2$, each r is independently 1 to 20, n=1-500, and m=1-500. Each of $R_2$ is selected from a (C1-C16)alkyl, a (C3-C16)cycloalkyl, a (C2-C16)alkenyl, a (C3-C16)cycloalkenyl, a (C2-C16)alkynyl, a (C3-C16)cycloalkynyl, or a (C6-C18)aryl.

Embodiment 18 is the modified polyisobutylene-based polymer of embodiment 17 wherein the phenoxy-containing polyisobutylene residues are derived from a phenoxy-containing polyisobutylene diol of the following formula:

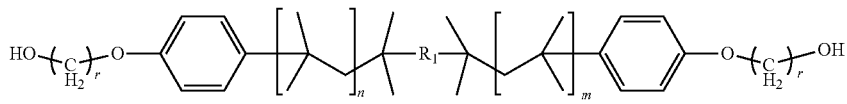

wherein $R_1$ is an initiator residue, each r is independently 1 to 20, n=1-500, and m=1-500.

Embodiment 19 is the modified polyisobutylene-based polymer of embodiment 18 wherein the phenoxy-containing polyisobutylene residues are derived from a phenoxy-containing polyisobutylene diol of the following formula:

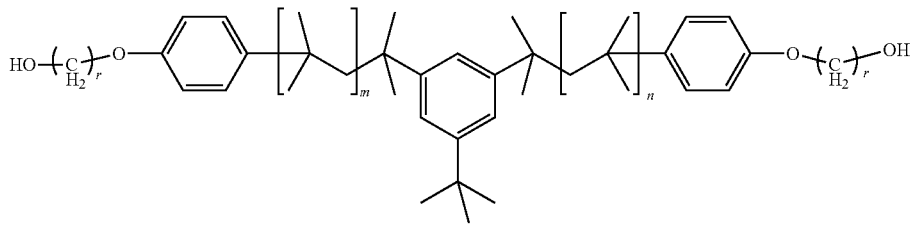

wherein each r (independently)=1-20, n=1-500, and m=1-500.

Embodiment 20 is the modified polyisobutylene-based polymer of any of the previous embodiments wherein the weight ratio of soft segments to hard segments is up to 90:10 (or up to 80:20, or up to 70:30).

Embodiment 21 is the modified polyisobutylene-based polymer of any of the previous embodiments wherein the weight ratio of soft segments to hard segments is at least 10:90 (or at least 30:70, or at least 40:60).

Embodiment 22 is the modified polyisobutylene-based polymer of embodiment 25 or 26 wherein the weight ratio of soft segments to hard segments is within a range of 90:10 to 10:90 (or within a range of 80:20 to 30:70, or within a range of 70:30 to 40:60).

Embodiment 23 is the modified polyisobutylene-based polymer of any of the previous embodiments having a weight average molecular weight of at least 10,000 Daltons, as determined by gel permeation chromatography with multiangle laser light scattering detection.

Embodiment 24 is the modified polyisobutylene-based polymer of any of the previous embodiments having a weight average molecular weight of up to 2,000,000 Daltons (or up to 1,000,000 Daltons), as determined by gel permeation chromatography with multiangle laser light scattering detection.

Embodiment 25 is the modified polyisobutylene-based polymer of embodiment 28 or 29 having a weight average molecular weight of 10,000 Daltons to 2,000,000 Daltons (or 10,000 Daltons to 1,000,000 Daltons), as determined by gel permeation chromatography with multiangle laser light scattering detection.

Embodiment 26 is a medical device comprising a polymeric region comprising the modified polyisobutylene-based polymer of any of the previous embodiments.

Embodiment 27 is the medical device of embodiment 31 comprising an implantable electrical lead, an implantable electrical pulse generator, or an implantable mechanical device.

Embodiment 28 is the medical device of embodiment 27 comprising an implantable electrical lead.

Embodiment 29 is the medical device of embodiment 28 wherein the implantable electrical lead comprises an electrical conductor and a layer comprising the modified polyisobutylene-based polymer disposed on the electrical conductor.

Embodiment 30 is the medical device of embodiment 28 or 29 wherein the electrical lead is a cardiac lead or a neurostimulation lead.

Embodiment 31 is the medical device of any of embodiments 26 through 30 wherein the polymeric region further comprises a therapeutic agent.

Embodiment 32 is a medical lead comprising an elongated lead body comprising a polymeric material, wherein the polymeric material comprises a modified polyisobutylene-based polymer of any of embodiments 1 through 25.

Embodiment 33 is the medical lead of embodiment 32 in the form of a medical electrical or neurological lead.

Embodiment 34 is a medical electrical lead comprising:
an elongated lead body having a first lumen, extending longitudinally along said lead body; and a conductor located within and extending longitudinally along said lumen;

wherein the lead body comprises a polymeric material, wherein the polymeric material comprises a modified polyisobutylene-based polymer of any of embodiments 1 through 25.

Embodiment 35 is a medical, neurological lead for use in electrical signaling and/or drug delivery comprising:

an elongated body with a distal portion, a central portion and a proximal portion;

wherein the body includes delivery means extending to said distal portion; and wherein the elongated body comprises a polymeric material, wherein the polymeric material comprises a modified polyisobutylene-based polymer of any of embodiments 1 through 25.

Embodiment 36 is the lead of embodiment 35 wherein the delivery means comprises electrical signal delivery means.

Embodiment 37 is the lead of embodiment 36 wherein the electrical signal delivery means is an implantable lead having at least one electrode.

Embodiment 38 is the lead of embodiment 35 wherein the delivery means comprises drug delivery means.

Embodiment 39 is the lead of embodiment 38 wherein the drug delivery means comprises a catheter.

Embodiment 40 is the lead of any of embodiments 35 through 39 wherein the polymeric material is a polymeric insulation material.

Embodiment 41 is a method of making a modified polyisobutylene-based polymer comprising phenoxy-containing polyisobutylene residues of any of embodiments 1 through 25, wherein the method comprises combining reactants comprising a diisocyanate, an optional chain extender, a phenoxy-containing polyisobutylene diol, damine, or combination thereof, and an optional additional soft segment-containing diol, diamine, or combination thereof under conditions effective to form the modified polyisobutylene-based polymer comprising phenoxy-containing polyisobutylene residues.

EXAMPLES

Objects and advantages of the disclosure are further illustrated by the examples provided herein. The particular materials and amounts thereof recited in these examples, as well as other conditions and details, are merely illustrative and are not intended to be limiting. The person of ordinary skill in the art, after carefully reviewing the entirety of this disclosure, will be able to use materials and conditions in addition to those specifically described in the examples.

Materials 4,4'-Methylenebis(phenyl isocyanate) (MDI, Aldrich, 98%), 1,4-butanediol (BDO, Aldrich, 99%), toluene (anhydrous, Aldrich, 99.8%), N,N-dimethylacetamide (DMAc, anhydrous, Aldrich, 99.8%), and 1-methyl-2-pyrrolidinone (NMP, anhydrous, Aldrich, 99.5%) were used as received.

Phenoxy-containing PIB diol can be made based on the previously reported method described in U.S. Pat. No. 8,344,073 (Storey et al.) Phenoxy-containing PIB diol was later converted into polyurethane in Example 1.

Characterization Methods

Nuclear Magnetic Resonance (NMR) experiments were conducted on Bruker Avance III HD spectrometer (400 MHz). Samples were dissolved in THF-$d_8$ for $^1$H or $^{13}$C NMR.

Molecular weights of polymers were determined via a size exclusion chromatography (SEC) system composed of an Agilent 1260 injection system, a Wyatt OPTILAB T-Rex refractive detector and a Wyatt DAWN Heleos II multiangle laser scattering detector. THF was the eluent. SEC was operated at 40° C. The data were processed by Astra 7.

Attenuated total reflection (ATR) Fourier-transform infrared spectroscopy (FTIR) experiments were conducted at ambient conditions on a Bruker Tensor 27 with a Ge crystal using 32 scans at a resolution of 4 $cm^{-1}$.

Reaction Scheme

Phenoxy-containing Polyisobutylene Diol and Corresponding Polyisobutylene Polyurethane

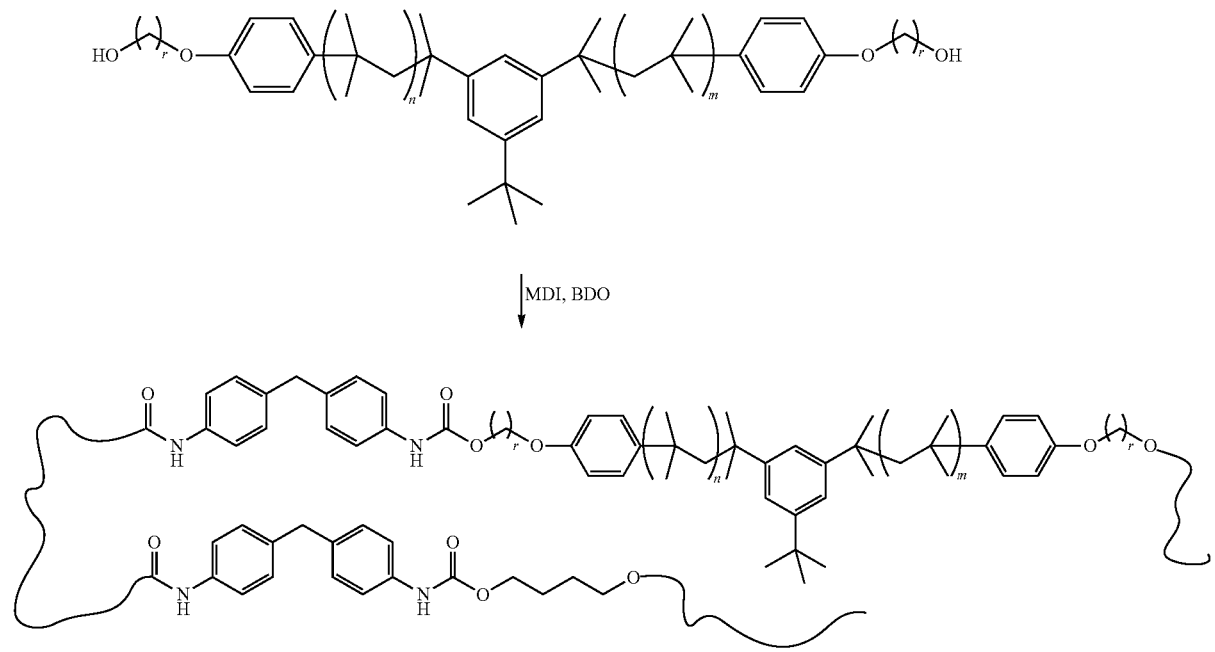

Example 1

Preparation of Polyurethane from Phenoxy-Containing Polyisobutylene

Polyurethane (PU) having phenoxy-containing PIB as soft segment and MDI/BDO as hard segment was synthesized using a prepolymer method. The ratio of soft segment to hard segment was 70:30. For example, a solution containing toluene (17 mL, anhydrous) and phenoxy-containing PIB diol (1.65 g, 0.3 mmol) was slowly added into a preheated flask (90° C.), which contained a stir bar and MDI (4.2 g, 16.8 mmol), under $N_2$ atmosphere. After all PIB diols reacted with MDI, a solution containing DMAc (40 mL, anhydrous) and BDO (1.1 g, 12.2 mmol) was then slowly added into the flask. The polymerization was then carried out at 100° C. for 20 hours. The PIB-PU products (17.0 g, yield: 95.5%) were precipitated from methanol and then dried in a vacuum oven at 50° C. NMR and FTIR confirmed the product was polyurethane. SEC showed $M_n$ 31 kg·mol$^{-1}$ and $M_w$ 52 kg·mol$^{-1}$.

The complete disclosures of the patents, patent documents, and publications cited herein are incorporated by reference in their entirety as if each were individually incorporated. Various modifications and alterations to this invention will become apparent to those of ordinary skill in the art without departing from the scope and spirit of this invention. It should be understood that this invention is not intended to be unduly limited by the illustrative embodiments and examples set forth herein and that such examples and embodiments are presented by way of example only with the scope of the invention intended to be limited only by the claims set forth herein as follows.

The invention claimed is:

1. A modified polyisobutylene-based polymer comprising urethane, urea, or urethane-urea groups, hard segments, and soft segments, wherein:

the soft segments comprise:
   phenoxy-containing polyisobutylene residues; and
   additional soft segment residues selected from poly(ether-carbonate) residues, polybutadiene residues, hydrogenated polybutadiene residues, polycarbonate residues, polyether residues, polyester residues, polysiloxane residues, and combinations thereof; and the hard segments comprise diisocyanate residues and chain extender residues.

2. The modified polyisobutylene-based polymer of claim 1 wherein the chain extender residues are derived from at least one chain extender selected from an aliphatic diol, an aromatic diol, an aliphatic diamine, an aromatic diamine, and a combination thereof.

3. The modified polyisobutylene-based polymer of claim 1 wherein the weight ratio of soft segments to hard segments is within a range of 90:10 to 10:90.

4. The modified polyisobutylene-based polymer of claim 1 wherein the weight ratio of phenoxy-containing polyisobutylene residues to additional soft segment residues is within a range of 99:1 to 1:99.

5. The modified polyisobutylene-based polymer of claim 1 having a weight average molecular weight of 10,000 Daltons to 2,000,000 Daltons, as determined by gel permeation chromatography with multiangle laser light scattering detection.

6. The modified polyisobutylene-based polyurethane of claim 1 wherein the additional soft segment residues are derived from a diol, a diamine, or a combination thereof.

7. The modified polyisobutylene-based polymer of claim 1 wherein the soft segments comprise phenoxy-containing polyisobutylene residues derived from a phenoxy-containing polyisobutylene diol, diamine, or a combination thereof.

8. The modified polyisobutylene-based polymer of claim 1 wherein the phenoxy-containing polyisobutylene residues are derived from a phenoxy-containing polyisobutylene compound of the following formula:

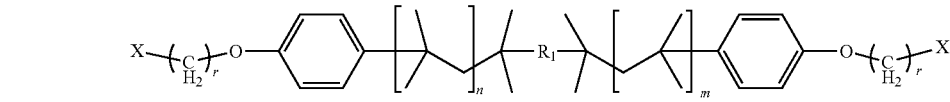

wherein $R_1$ is an initiator residue, each X is independently —OH, —$NH_2$, or —$NHR_2$, each r is independently 1-20, n=1-500, and m=1-500.

9. The modified polyisobutylene-based polymer of claim 1 wherein the phenoxy-containing polyisobutylene residues are derived from a phenoxy-containing polyisobutylene diol of the following formula:

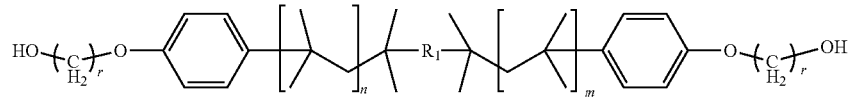

wherein $R_1$ is an initiator residue, each r is independently 1-20, n=1-500, and m=1-500.

10. The modified polyisobutylene-based polymer of claim 1 wherein the phenoxy-containing polyisobutylene residues are derived from a phenoxy-containing polyisobutylene diol of the following formula:

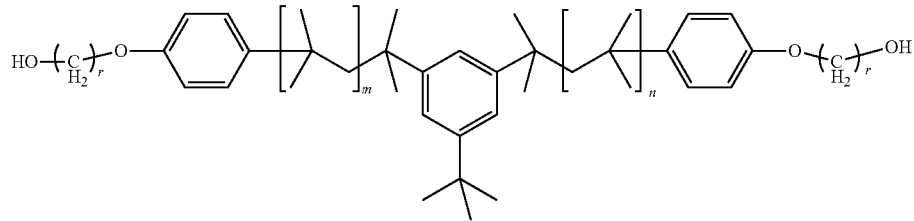

wherein each r (independently)=1-20, n=1-500, and m=1-500.

11. A medical device comprising a polymeric region comprising a modified polyisobutylene-based polymer comprising urethane, urea, or urethane-urea groups, hard segments, and soft segments, wherein:
the soft segments comprise:
  phenoxy-containing polyisobutylene residues; and
  additional soft segment residues; and
the hard segments comprise diisocyanate residues.

12. The medical device of claim 11 wherein the additional soft segment residues are selected from poly(ether-carbonate) residues, polybutadiene residues, hydrogenated polybutadiene residues, polycarbonate residues, polyether residues, polyester residues, polysiloxane residues, and combinations thereof.

13. The medical device of claim 11 wherein the hard segments further comprise chain extender residues.

14. The medical device of claim 11 wherein the weight ratio of soft segments to hard segments is within a range of 90:10 to 10:90.

15. The medical device of claim 11 wherein the weight ratio of phenoxy-containing polyisobutylene residues to additional soft segment residues is within a range of 99:1 to 1:99.

16. The medical device of claim 11 comprising an implantable electrical lead, an implantable electrical pulse generator, or an implantable mechanical device.

17. The medical device of claim 16 comprising an implantable electrical lead.

18. The medical device of claim 11 wherein the polymeric region further comprises a therapeutic agent.

* * * * *